US007722856B2

(12) United States Patent
Browitt et al.

(10) Patent No.: US 7,722,856 B2
(45) Date of Patent: May 25, 2010

(54) PROCESS FOR THE PRODUCTION OF A RADIOACTIVE AEROSOL

(75) Inventors: Rodney James Browitt, Kaleen (AU); William Martin Burch, Gymea Bay (AU); Timothy John Senden, Aranda (AU); Ross Wentworth Stephens, Stirling (AU); David DeForest Shaw, Chandler, AZ (US)

(73) Assignee: Cyclomedica Australia Pty Limited, Lucas Heights (AU)

( * ) Notice: Subject to any disclaimer, the term of this patent is extended or adjusted under 35 U.S.C. 154(b) by 0 days.

(21) Appl. No.: 11/361,602

(22) Filed: Feb. 24, 2006

(65) Prior Publication Data

US 2007/0009430 A1    Jan. 11, 2007

(30) Foreign Application Priority Data

Jul. 11, 2005    (AU)    ................................ 2005903674

(51) Int. Cl.
*A61B 6/00*        (2006.01)
*A61K 49/00*    (2006.01)
(52) U.S. Cl. .................................................. 424/1.11
(58) Field of Classification Search ................ 424/1.1, 424/1.13, 1.11, 46
See application file for complete search history.

(56) References Cited

U.S. PATENT DOCUMENTS 5,064,634 A * 11/1991 Burch ........................ 424/1.13
5,228,444 A * 7/1993 Burch ........................ 600/431
5,792,241 A    8/1998 Browitt
2004/0136904 A1 * 7/2004 Pitcairn ..................... 424/1.11

FOREIGN PATENT DOCUMENTS

| EP | 0181092 A2 | 5/1986 |
| WO | 00/48202 A1 | 8/2000 |
| WO | 2007/006071 A1 | 1/2007 |

OTHER PUBLICATIONS

Tim J. Senden et al., "The Physical and Chemical Nature of Technegas", The Journal of Nuclear Medicine, vol. 38, No. 8, Aug. 1997, pp. 1327-1333.
Search Report issued in corresponding European Patent Application Serial No. 06004363.5.
M. V. Mikelsons et al., "A Carbon Particulate, Packed Bed Electrolysis Flow Cell for the Production of Technetium Complexes," International Journal of Radiation Applications and Instrumentation Part A, Applied Radiation and Isotopes, vol. 37, No. 9, 1986, pp. 991-994.
James S. Brown et al, "Generation of Radiolabeled "Soot-Like" Ultrafine Aerosols Suitable for Use in Human Inhalation Studies," Aerosol Science and Technology, vol. 32, No. 4, Apr. 2000, pp. 325-337.

* cited by examiner

*Primary Examiner*—Michael G Hartley
*Assistant Examiner*—Jagadishwar R Samala
(74) *Attorney, Agent, or Firm*—Pearne & Gordon LLP (57) ABSTRACT

A method for forming an inhalable isotope compound suitable for use in patient medical diagnosis, the method comprising the steps of: (a) electrolytic loading of a carbon crucible with the isotope; (b) sublimating any isotope carrier in the crucible; (c) ablating the isotope in a carbon crucible, forming an ablation aerosol; (d) directly delivering the aerosol for immediate use by a patient. The isotope can comprise technetium.

21 Claims, 6 Drawing Sheets

PROCESS FOR THE PRODUCTION OF A RADIOACTIVE AEROSOL

FIELD OF THE INVENTION,

The present invention relates to the production of inhalable isotope compounds (including technetium chemical compounds, or composites and mixtures) and, in particular, discloses improved methods for their production.

BACKGROUND OF THE INVENTION

Any discussion of the prior art throughout the specification should in no way be considered as an admission that such prior art is widely known or forms part of common general knowledge in the field.

This invention relates to a method for production of a radioactive aerosol such as carbon-encapsulated technetium-labelled nanoparticle-composites that can be used in medical diagnostics for gamma scintigraphy imaging of the interior of the lungs of a patient suffering from an airway dysfunction. Methods for production of carbon-encapsulated technetium-labelled nanoparticle-composites are well known.

U.S. Pat. No. 5,064,634 to Burch entitled "Method of Forming a Radioactive Metallic Vapor" and U.S. Pat. No. 5,228,444 to Burch entitled "Device for Producing a Gas-Lite Radionuclide Composition" discloses a method and apparatus for production of such inhalable radionuclide labelled aerosols. In particular, there is described a carbon crucible heated to a temperature within the range of 1500° to 2500° Celsius. The resulting aerosol product was later found to consist of the nanoparticle-composite described by Senden et al, (J. Nuclear Med. 38:1327-33, 1997) who also reported on incorporation of other isotopes. The product has been found suitable for use as a radioactive aerosol that can be used in medical diagnostics for gamma scintigraphy imaging of the interior of the lungs of a patient suffering from an airway dysfunction.

U.S. Pat. No. 5,792,241 to Browitt entitled "Precipitator" discloses a method and apparatus for dispersing the nanoparticle-composite into an aqueous medium.

The methods of production of carbon-encapsulated technetium-labelled nanoparticle-composites in the above prior art have a number of disadvantages.

1) The method of loading of the generator's carbon crucible with radionuclide is typically limited to evaporation of a radionuclide solution or direct addition of a solid. Using vapour phase particle sizing with appropriate instrumentation it has now been unfortunately and surprisingly found that both of these methods give rise to considerable contamination of the aerosol with large (>200 nm diameter) sodium chloride particles originating from the saline solution used to elute technetium generators. Salt contamination can be particularly significant when multiple loadings of the crucible are employed to concentrate the radionuclide eluate of weaker or older technetium generators. Multiple loading (e.g. three times or more) is often used in the clinical setting, especially in countries where only low specific activity technetium generators (e.g. 60 GBq) are available. Clearly sodium chloride particles are water soluble and therefore rapidly dissolve on wet surfaces such as lung airways, and may be carriers of non-encapsulated technetium in soluble form. This can lead to poor imaging of the lungs.
2) Using the conditions as described in the prior art was found to produce aerosols contaminated with surprisingly large amounts of water-soluble free radionuclide. This is a result of the rapid sublimation of the more volatile sodium chloride expelling radionuclide from the crucible before carbon encapsulation occurs. Non-encapsulated radioactive contaminants in the aerosol can lead to the disadvantageous result that they dissolve on the surface of a patient's lungs and subsequently enter the blood circulation and lymphatics. It can be reasonably expected that contamination with soluble free radionuclide will degrade the quality of airway imaging, by diffusion of signal away from the inner surface of the lungs, thus decreasing the specific signal to noise ratio. More importantly, it also unnecessarily exposes the patient to a significant systemic dose of radionuclide that continues for some hours after the imaging procedure.
2) In U.S. Pat. No. 5,064,634, the disclosed enabling conditions for aerosol generation have been found to produce poor results. It is conjectured that resistive heating of the carbon crucible is not sufficient to yield optimal amounts of a suitable imaging product.
3) The only description given in U.S. Pat. No. 5,064,634 relating to the method of heating the crucible is that it should be heated "preferably to at least 2200° C.". It has been found that particles formed using this temperature range as a guide can be contaminated with free radionuclide, again leading to image degradation and systemic dosing. Further, larger particles (>200 nm diameter) of unstructured carbon were found to form at some higher temperature ranges. Larger particles can be expected to give less favourable airway imaging, penetrating less distance into the lungs before adhering to airway surfaces.
4) The duration of crucible heating in the generator is not specified in U.S. Pat. No. 5,064,634, nor is the time the aerosol product is allowed to reside in the apparatus before inhalation by the patient. It has been found that these factors are critical in particle production.

SUMMARY OF THE INVENTION

It is an object of the present invention to provide an improved method for creating a radioactive aerosol.

In accordance with a first aspect of the present invention, there is provided a method for forming an inhalable isotope compound suitable for use in patient medical diagnosis, the method comprising the steps of: (a) electrolytic loading of a carbon crucible with the isotope; (b) sublimating any isotope carrier in the crucible; (c) ablating the isotope in a carbon crucible, forming an ablation aerosol; (d) directly delivering the aerosol for immediate use by a patient.

Preferably, the isotope can comprise technetium. Preferably, the electrolytic flow transitioning the crucible can be between substantially 0.1 to 0.7 mL per minute. The current through the electrolytic cell can be substantially between 1 and 10 milliamps. The duration of the electrolysis can be substantially between 10 and 60 minutes.

Preferably, the isotope carrier can comprise a salt, ideally sodium chloride. The sublimation can occur in an argon atmosphere. The sublimation occurs in an argon atmosphere purging a chamber for substantially between 2 and 10 minutes. Preferably, the temperature for sublimation occurs at substantially 1200 to 1800 degrees Celsius. The duration of the sublimation can be substantially between 10 and 20 seconds.

Preferably, the ablation occurs in an argon atmosphere. The temperature rise time for ablation can be substantially 0.3 to 0.7 seconds. The temperature of the ablation can be substantially between 2740 and 2780 degrees Celsius. The ablation can occur for substantially between 2.5 and 3.5 seconds. The ablated isotope aerosol can be delivered directly to a patient for medical imaging.

Further, the aerosol can be periodically subjected to capture in water and analysed to determine the operational efficiency of the method. The analysis preferably can include analysis of free pertechnetate levels or excess carbon levels.

In accordance with a further aspect of the present invention, there is provided a method for forming an inhalable isotope compound suitable for use in patient medical diagnosis, the method including at least one of the following steps: (a) electrolytic loading of a carbon crucible with the isotope; (b) sublimating any isotope carrier in the crucible; and (c) ablating a previously sublimated isotope in a carbon crucible, forming an ablation aerosol.

Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

BRIEF DESCRIPTION OF THE DRAWINGS

A preferred embodiment of the invention will now be described, by way of example only, with reference to the accompanying drawings in which.

DESCRIPTION OF THE PREFERRED AND OTHER EMBODIMENTS

The preferred embodiments of the present invention provide for a substantial improvement of radioactive aerosols suitable for use in imaging patient airways.

The preferred embodiment involves a multistage process for carefully controlling the production of an optimised lung imaging agent, comprising an aerosol of stable radioactive nanoparticles that are substantially water insoluble. The preferred embodiment has been derived in part from extensive use of vapour phase particle sizing and liquid phase physicochemical analysis to enable close specification of the precise conditions enabling commercial production of an aerosol that is particularly suitable for diagnostic medical imaging and represents a considerable improvement on the prior art. The preferred embodiment also preferably includes innovative methods for quality control of the imaging product.

The preferred embodiment addresses the following issues:

1) Electrolytic Crucible Loading

The level of water-soluble sodium chloride and free non-encapsulated radionuclide (i.e. pertechnetate) contaminating the aerosol must be minimised. Surprisingly, it has been found that this can be achieved by using a novel method of crucible loading, employing electrolytic concentration of the radionuclide. It has also been found that evaporative loading of crucibles in standard prior art carbon-encapsulated technetium-labelled nanoparticle-composite creation devices may produce pertechnetate contamination levels of over 20% of the total aerosol radioactivity, and may be as high as 60% of the radioactivity in the aerosol delivered to the patient. By contrast, it has been found that non-encapsulated pertechnetate contamination can be reduced to less than 6% by electrolytic loading of crucibles.

Electrolytic loading also permits the direct use of isotope from weaker technetium generators as well as the extended use of standard technetium generators by providing a method for the concentration of radionuclide in a carbon crucible without increasing sodium chloride loading of the crucible. Extended use of standard isotope generators in turn provides a considerable cost savings in the hospital purchasing of radioisotope.

2) Sublimation of Carrier Sodium Chloride

Heating of the crucible in two stages has been found advantageous in reducing soluble sodium chloride contamination of aerosol; during the first stage, the crucible is raised to a temperature suitable for sublimation of carrier sodium chloride (e.g. 1685° C.) and in the second stage, the crucible is held at a temperature suitable for plasma ablation of the radionuclide from the crucible (e.g. 2775° C.). The first stage heating has a relatively slow rise time of approximately 1 second to reach 1685° C. and is held at that temperature for a period of between 5 and 20 seconds to effect the sodium chloride sublimation. During this phase, the vapour-phase sodium chloride is continuously removed by concurrent argon purging to a safety purge filter.

3) Temperature Rise Time Control

The enabling conditions for appropriate crucible ablation are more complex than merely heating of the crucible to a particular temperature. Specifically, the time it takes for the crucible to reach the desired temperature is critical. Furthermore, the conditions within the crucible chamber must be permissive for the induction and maintenance of an alternating current (AC) plasma at that temperature. The AC plasma is necessary to ablate and encapsulate radionuclide particles from the crucible surface with carbon. Merely heating the radionuclide in a carbon crucible will not produce a product suitable for imaging. The preferred embodiment provides for thermionic induction of plasma across the opening of the crucible, not merely resistive heating of the body of the crucible. This condition is satisfied through the use of a microprocessor-regulated AC power supply that produces an extremely rapid rise-time (approximately 0.4 seconds) in the crucible thermoprofile to full ablation temperature. Induction of plasma is also enhanced by the presence of sodium ions and the argon purge gas (i.e argon readily ionises at high temperatures).

4) Ablation Temperature Control

The size of carbon-encapsulated nanoparticles in the aerosol produced by plasma ablation of the graphite crucible—at least over the range of 2600-2900° C.—is a direct function of the ablation temperature. The optimal crucible ablation temperature range for formation of an aerosol of carbon-encapsulated technetium particles of less than 100 nm diameter is in the range of 2760±20° C. This temperature range produces substantial quantities of water-insoluble carbon-encapsulated radionuclide nanoparticles with a peak size of approximately 90 nm diameter, i.e. small enough to favour deep lung penetration after inhalation. These nanoparticles do not release appreciable soluble radionuclide on contact with water, even under autoclave conditions. The purging of the generator with argon is critical for plasma formation of these small particles as the presence of oxygen is thought to selectively destroy the smallest particles.

From vapour phase particle analysis it has now been found that the size of particles produced in the aerosol is a direct function of crucible ablation temperature, and that carbon-encapsulated particles suitable for imaging (<150 nm diameter) are produced in a narrow temperature range that is 500-600° C. higher than previously specified.

5) Ablation Timing Control

To produce sufficient encapsulated particles without production of excess carbon, the optimal duration of crucible ablation at 2760±20° C. has been determined. Under the described crucible ablation conditions above, thermionic plasma ablation of radionuclide occurs very rapidly and prolonged heating only produces more unwanted carbon in the aerosol. The optimum duration of plasma ablation at 2760±20° C. is approximately 2.5 to 3.5 seconds.

Thermionic induction of plasma is required across the opening of the crucible, which subsequently ablates an aerosol of carbon and radionuclide particles from the crucible surface. This is evidenced by:
  a) the marked increase in carbon particle aerosol output from a sodium chloride treated crucible compared to an untreated crucible; even trace amounts of sodium ions are well known to promote thermionic emission,
  b) the marked increase in conductivity of a loaded crucible above 1800° C., consistent with arcing through an ionised gas (argon is easily ionised),
  c) visible changes in the crucible surface produced by the arcing.

6) Immediate Availability for Aggregate Reduction

Surprisingly it has been found that aggregation of encapsulated particles in the aerosol is very rapid and pronounced. The time scale involved is seconds rather than minutes. Accordingly, in the preferred embodiments, the carbon-encapsulated technetium-labelled nanoparticle-composite aerosol is immediately available to the patient from the crucible's particle emission in the generator. The duration of crucible heating is kept very short and ideally the particles emitted from the crucible continuously collected in flowing argon and delivered to the patient on line, without any delay in the crucible chamber. Although the crucible temperature is very high, there are no issues of heat of the aerosol involved for the patient—the temperature of the output aerosol after passage through the generator/delivery system is close to room temperature.

A further justification for direct delivery of the aerosol is that vapour phase aggregation not only rapidly accumulates radioactivity in larger particles, it also markedly diminishes the fraction of radioactivity present as smaller particles. It is the smaller aerosol particles that provide the best imaging of the lung's extremities, not the larger. Larger particles stay higher in the airways and do not penetrate the furthest extremities of the lungs. It follows that less radionuclide may be required for each lung image if a higher proportion of radionuclide can be delivered to the lungs as smaller insoluble particles. Furthermore, any reduction in patient exposure to radioactivity resulting from larger particles is advantageous for the minimisation of complications in the patient as a result of the imaging procedure.

The size of the aerosol particles increases rapidly due to aggregation, and large aggregated particles quickly settle out of the aerosol onto the interior of the chamber. Thus, while a large proportion of radioactivity is initially present in small aerosol particles well suited for lung imaging, within 3 minutes this radioactivity is lost to the chamber walls of the generator device. The aerosol released after retention in the chamber for more than a few minutes is in fact enriched in water-soluble sodium chloride and free radionuclide particles.

7) Quality Control

To provide monitoring of the normal functioning of the aerosol generation, quality control methods have been incorporated into the device. This aids in maintaining the uniform suitability of the aerosol product for diagnostic lung imaging. Other systems that do not incorporate these or similar quality control measures present the risk that patients are not receiving an optimal imaging dose whilst also minimising post-procedure systemic exposure.

The preferred embodiment therefore also includes periodic testing of the aerosol product by capture of the carbon-encapsulated radionuclide nanoparticles in an aqueous dispersion by the use of an electrostatic sonicating precipitator (such as that disclosed in U.S. Pat. No. 5,792,241). The captured particles are then available as a stable aqueous dispersion suitable for analysis of at least free pertechnetate (thin-layer chromatography method) and excess carbon (light-scattering method). These simple tests use reference baseline data from a database of carefully controlled generator runs that the current measurement is compared against.

Overview Of New Carbon-Encapsulated Technetium-Labelled Nanoparticle-Composite Creation Process The aerosol production process of the preferred embodiment consists of the following three stages:
  1) Graphite crucible loading by electrolytic deposition of radionuclide in a purpose-built concentrator device.
  2) Preheating of the crucible with argon purging in a modified generator to remove sodium chloride by sublimation at a temperature below the boiling point of the radionuclide.
  3) Plasma ablation of carbon-encapsulated radionuclide particles from the graphite crucible using a tightly controlled thermoprofile, and with continuous argon gas flow directed on line to the patient.

This three stage process above includes several substantial departures from the prior art technology as follows:

Stage 1

The loading of radionuclide into the graphite crucible is now accomplished by the use of an electrolytic concentrator. In the standard carbon-encapsulated technetium-labelled nanoparticle-composite creation process the crucible is typically loaded by simply evaporating one or more loadings of a solution of radionuclide in the crucible. Electrolytic loading of crucibles has surprisingly been found to achieve aerosol preparations that have a lower contamination of water-soluble sodium chloride and free (non-encapsulated) radionuclide (as water-soluble pertechnetate).

Stage 2

The carbon-encapsulated technetium-labelled nanoparticle-composite generator design has been modified and the graphite crucible heating conditions changed to provide a pre-heating sub-routine. The pre-heating removes sodium chloride from the loaded crucible by sublimation at 1685° C. into an argon purge stream. The sublimated sodium chloride is captured in a purge filter.

Stage 3

The carbon-encapsulated technetium-labelled nanoparticle-composite generator design has been modified and the crucible ablation conditions changed to permit:

Elimination of air traps in the crucible chamber and allow stratified argon purging of the crucible chamber so as to efficiently remove all traces of air prior to crucible heating.

Addition of controls which enable two stage heating as above with continuous argon gas flow during sodium chloride sublimation and during plasma ablation of the crucible.

A modified thermoprofile for crucible ablation—it is required in the preferred embodiments that the crucible temperature rises sharply through the 2000° C. to 2800° C. range, preferably in approximately 0.4 seconds.

Tightly regulated temperature control of crucible plasma ablation to achieve the optimal ablation temperature range of 2750° C. to 2780° C. with a stability of ±15° C.

Reduced the duration of crucible ablation from 15 seconds to 2.5-3.0 seconds.

Process Flowchart

Figure 1:
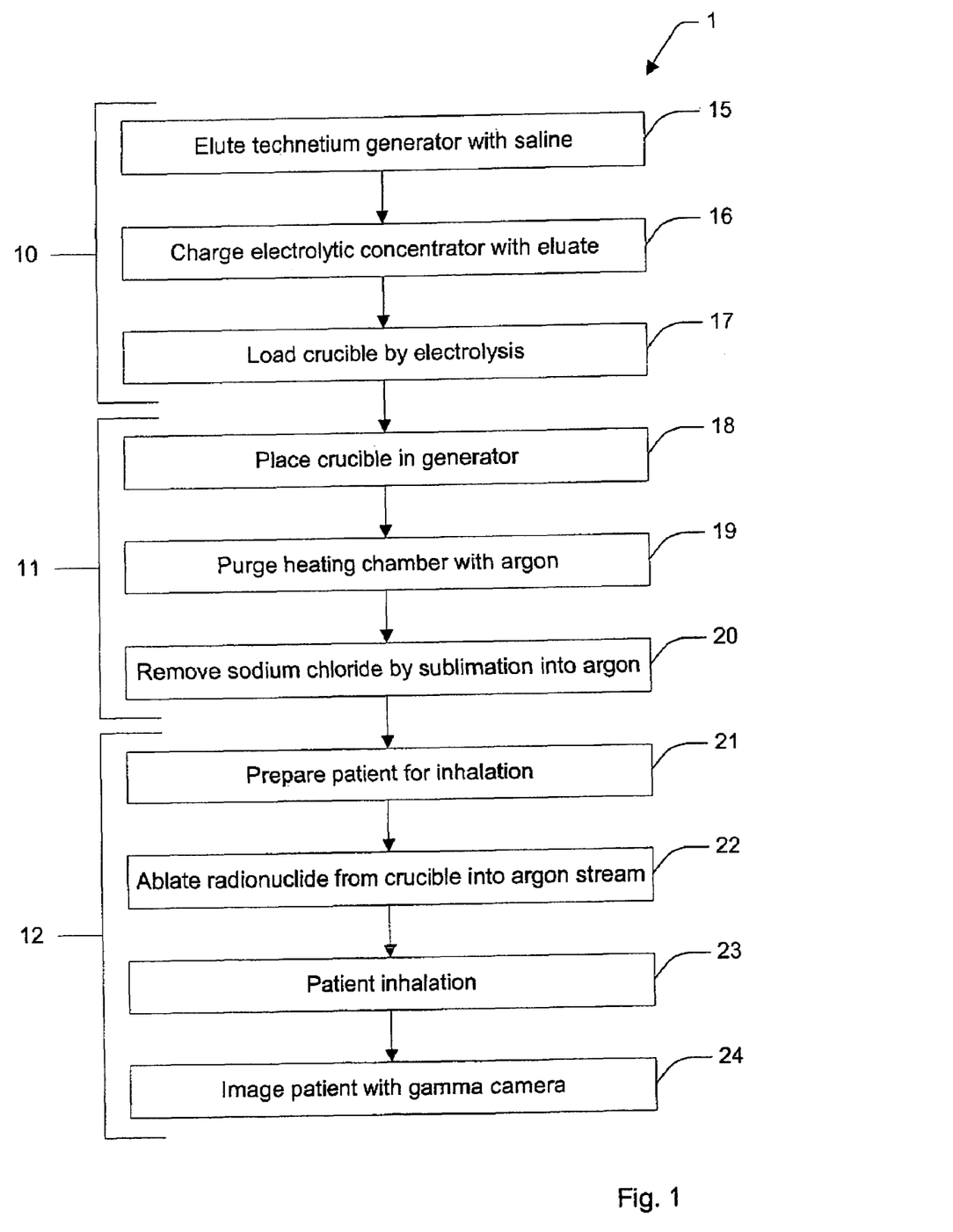
FIG. 1 illustrates a flowchart of the steps of the preferred embodiment.

Turning initially to FIG. 1 there is illustrated a flowchart 1 of the steps involved in the preferred embodiment.

The preferred embodiment consists of core steps 10 and 11, each of which is divided into a series of substeps. The first step 10 deals with crucible loading, and the second step 11 with preparation of the crucible. The third step 12 in the process is related to preparation of the patient for the imaging procedure.

Crucible Loading 10

The crucible loading step 10 consists of three sub steps including the elution of a technetium generator with saline 15, charging an electrolytic concentrator with the elute 16 and loading a crucible by electrolysis 17.

The crucible has the following desirable characteristics:

The crucible material is preferably of a high purity graphite, such as that designated by product number G347S manufactured by the Tokai Carbon Co Ltd of Japan.

The preferred crucible dimension is approximately 32 mm long×6.35 mm wide by 6.35 mm high. A variety of crucible sizes can be used, but it is limited by the ability of the generator machine to electrically heat the crucible to the right temperature fast enough and to initiate and sustain the necessary plasma ablation conditions. The ultimate limiting factor is the current drawn from the mains power supply by the generator, which typically must be less than 20 amperes.

The crucible volume may extend over a range of up to 300 microlitres. The small oval crucibles and larger hexagonal and oval crucibles used to obtain the results described herein had a volume of between 100 microlitres and to about 140 microlitres. The crucible volume is limited only by the generator's ability to drive the higher resistance of the larger volume crucible.

The crucible shape is primarily intended to concentrate heat production (i.e the electrical resistance) in the central part of the crucible. To achieve this, the crucible walls are milled thinner than the end contacts and the stems.

The crucibles are ultrasonically cleaned before use to remove adherent graphite particles formed during the milling process.

Figure 2A:
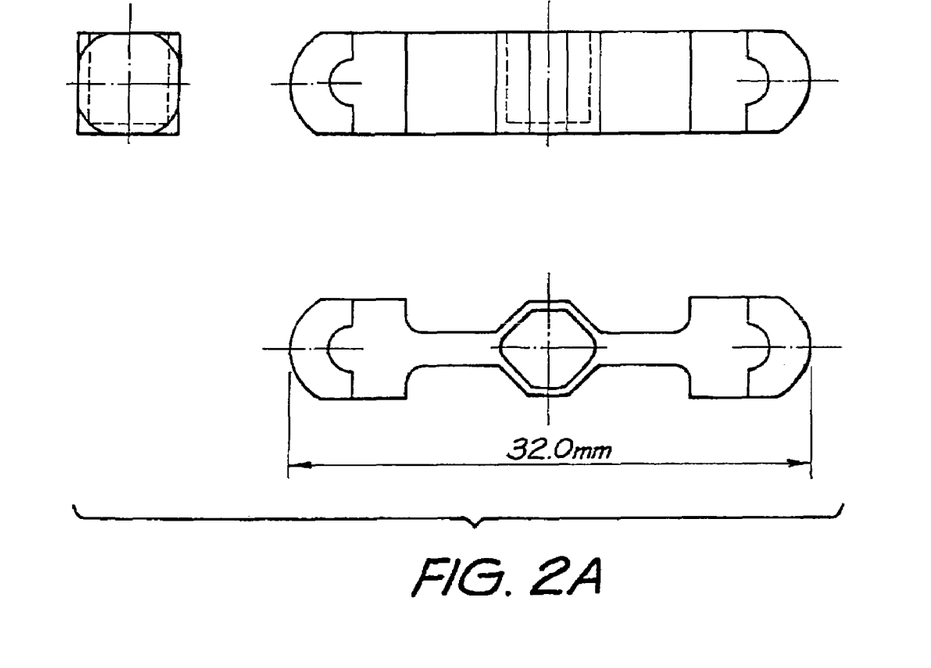
FIGS. 2A and 2B illustrate various plan views of alternative crucible designs.
Figure 2B:
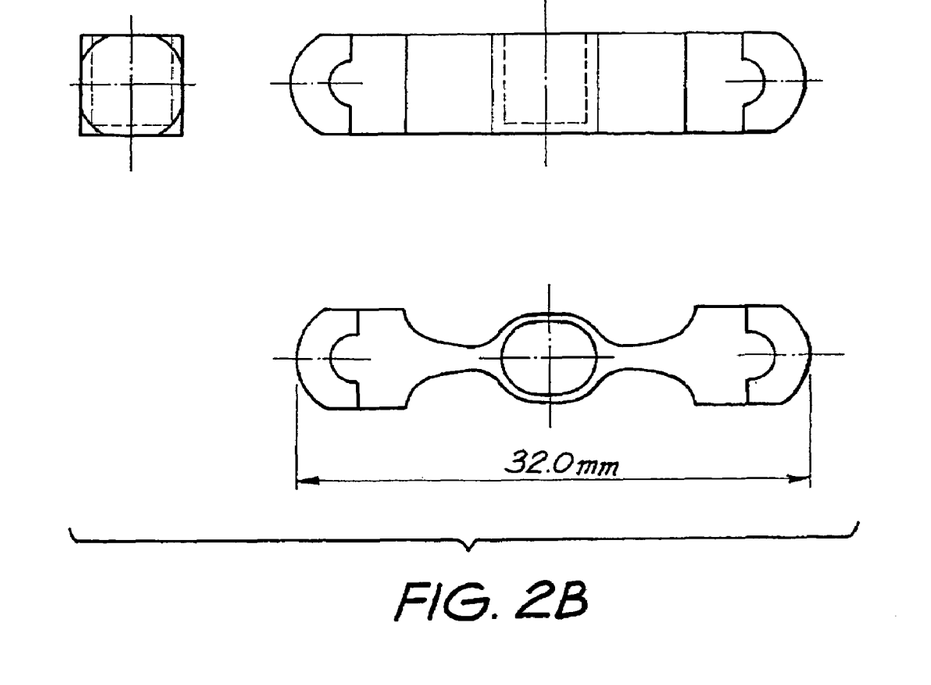

Initially, a technetium isotope is obtained in the form of a sodium pertechnetate eluted with saline from the alumina matrix of a molybdenum-decay generator, which is the standard commercial method of obtaining technetium isotope. The technetium is next concentrated in a carbon crucible by an electrolytic concentrator method. Example carbon crucibles can be shaped as shown in FIG. 2A and FIG. 2B.

The electrolytic concentrator method enables the isotope to be sourced from technetium generators with a low elute activity. The nanoparticles produced from this method have a level of pertechnetate contamination of less than 6%, which is lower than evaporative methods of nanoparticle production.

Figure 3:
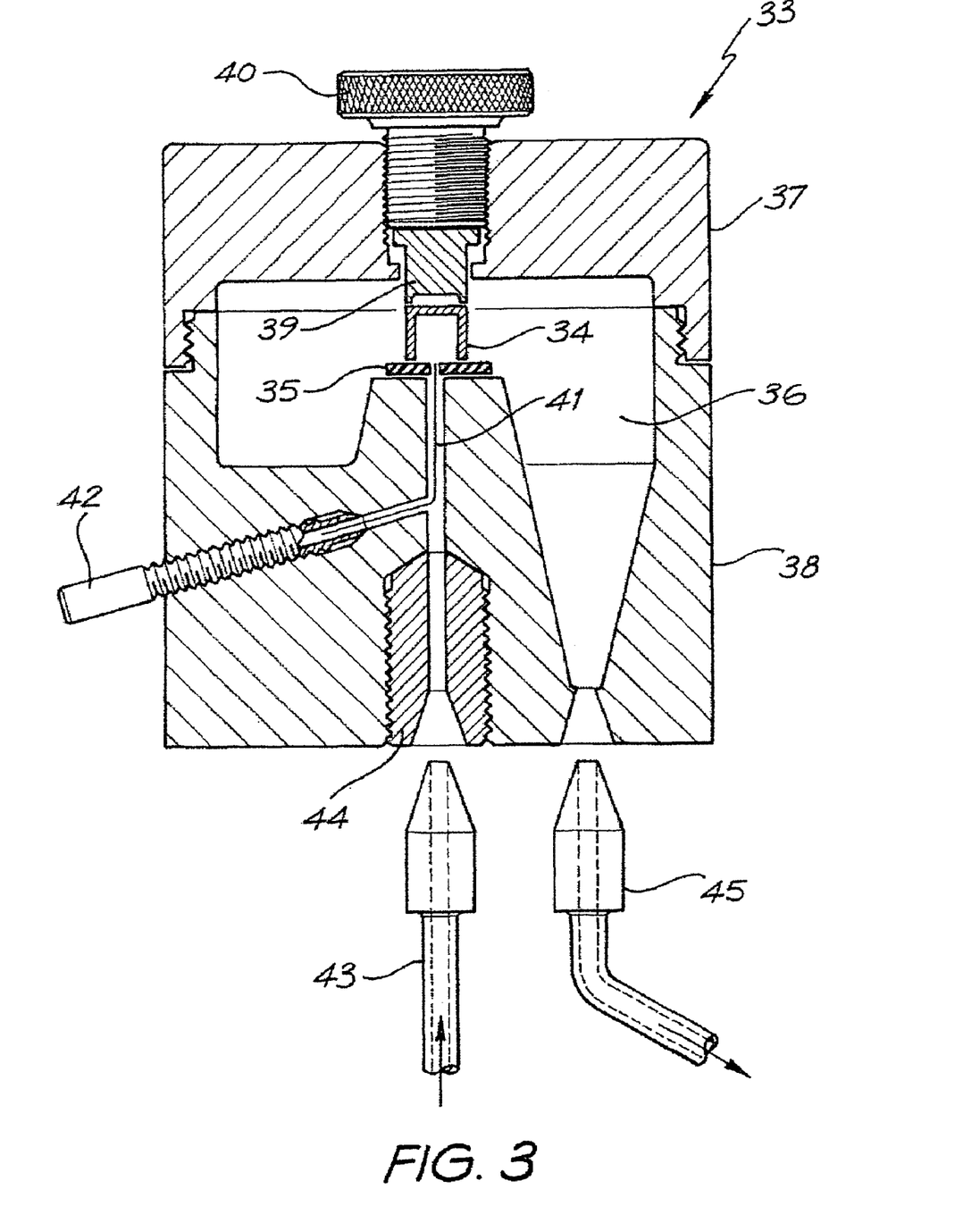
FIG. 3 is a sectional view of the electrolytic concentrator.

FIG. 3 is a sectional view of one form of suitable electrolytic concentrator 33 for use with the elution. A crucible 34 forms the cathode of the concentrator and is placed on a silicone rubber gasket 35 inside a chamber 36 formed from two mating parts 37, 38. The crucible is held in place by means of a stopper 39 and a pressure adjusting screw 40. The anode of the cell consists of a fine platinum wire 41 which runs up the centre of the fluid delivery tube. The tube is in communication with a Luer tapered liquid input tube 43 via a polycarbonate insert 44. The saline isotope solution is pumped into the chamber 36 and exits via Luer output taper 45 to a reservoir where it is recirculated. The outer shell 37, 38 can be formed from Teflon or Teflon coated materials.

Figure 4:
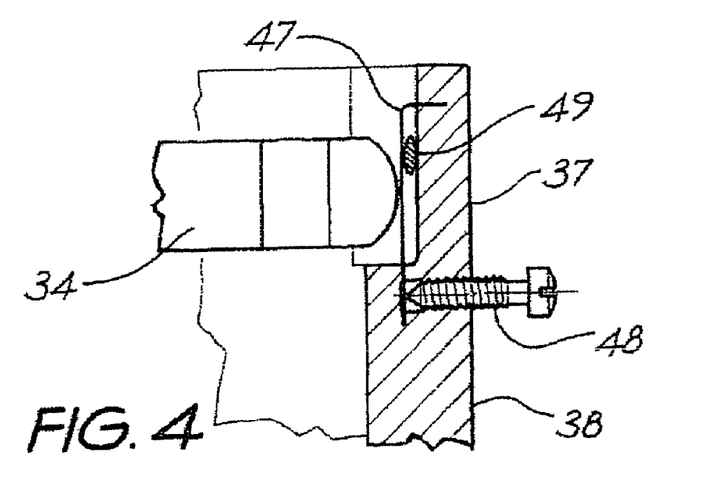
FIGS. 4 and 5 illustrate close up section views of portions of the electrolytic concentrator.
Figure 5:
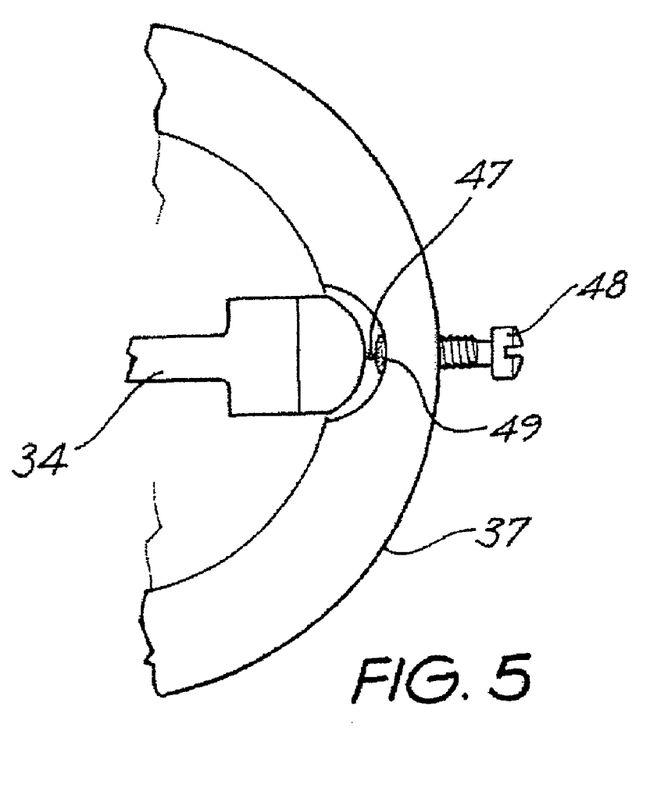

FIG. 4 and FIG. 5 illustrate the formation of the crucible cathode in more detail with FIG. 4 illustrating a side view and FIG. 5 illustrating a top view. The crucible 34 is interconnected to a platinum wire contact 47 which is held in place against the crucible by silicone rubber 49. The wire is attached to contact screw 48 which forms the negative power supply input.

Typical operating parameters are shown in Table 1 below:

TABLE 1

| PROCESS COMPONENT | PARAMETER | RANGE | PREFERRED VALUE |
|---|---|---|---|
| Concentrator loading | Electrolyte flow transiting crucible | 0.1-0.7 mL/min | 0.33 mL/min |
| | Constant current through electrolytic cell | 1-10 mA | 5 mA |
| | Duration of electrolysis | 10-60 min | 30 min |

The saline eluate from a technetium generator is circulated continuously through the walls of a porous graphite crucible under the pressure of a peristaltic pump. The crucible 34 forms the cathode of an electrolytic cell and the anode consists of the fine platinum wire 44 placed in the opening of the crucible. Radionuclide is deposited on the graphite surface inside the crucible opening. The accumulation of radionuclide in the crucible may be conveniently monitored by the loss of radioactivity from the circulating liquid, e.g. with a Geiger counter placed over a few loops of the tubing circuit 46.

Utilising the disclosed arrangement as an electrolytic concentrator, the technetium is concentrated onto the inner surface of the graphite crucible by the combined action of the electrolysis and the continuous pumping of the saline isotope solution.

Crucible Preparation 11

Returning to FIG. 1, the crucible preparation step 11 include the sub-steps of placing the crucible in the generator 18, purging the heating chamber with argon 19 and removing sodium chloride by sublimation.

It has surprisingly been found that a carefully controlled preheating step after crucible loading and prior to particle generation has a marked effect on the nature of the nanoparticles subsequently plasma ablated from the crucible at a higher temperature. During the preheating step, a carrier, typically sodium chloride is removed, preferably by evaporation into a flow of inert gas such as argon that is held at a suitable temperature and for a predetermined time. The conditions outlined in Table 2 below have been found to be suitable for efficient sodium chloride sublimation. For other carriers the protocol can be followed with suitable variation of the rise time and the temperature. The boiling point of the carrier must be lower than the temperature range that leads to loss of isotope from the crucible.

TABLE 2

| PROCESS COMPONENT | PARAMETER | RANGE | PREFERRED VALUE |
|---|---|---|---|
| Pre-heating of crucible for removal of sodium chloride | Argon purge of crucible chamber - flow rate | 6-14 litres/min | 8 litres/min |
| | Argon purge of crucible chamber - duration | 3-10 min | 6 min |
| | Crucible temperature rise time for sodium chloride sublimation | 0.8-1.5 secs | 1.0 sec |
| | Temperature for sodium chloride sublimation from crucible | 1200-1800° C. | 1685° C. |
| | Duration of sodium chloride sublimation from crucible | 5-20 secs | 10 secs |

The preferred operating conditions given in Table 2, namely 1685° C. for 10 seconds provide for the sodium chloride evaporation by crucible heating and inert gas purging. The process is preferably carried out in a suitably modified device of the type such as that disclosed in U.S. Pat. No. 5,064,634. It has not previously been appreciated that the duration of the preheating step effects such parameters as:

1. Carbon emission from the crucible during plasma ablation. Preheating the crucible for at least 5 seconds at a temperature above the boiling point of sodium chloride (e.g. 1685° C.) but below the temperature used to induce thermionic plasma (e.g. 2750° C.) was found to markedly reduce the amount of free carbon subsequently ablated from the crucible.
2. Pertechnetate contamination levels of the nanoparticle dispersion. Preheating of the crucible for at least 5 seconds produces a significant reduction in the level of water-soluble pertechnetate label contaminating the nanoparticle dispersion. Nanoparticles produced after sufficient preheating of the crucible have greater stability in the presence of heat, that is, less free pertechnetate label is released into solution from these nanoparticle suspensions during autoclaving.

Plasma Ablation

Figure 6:
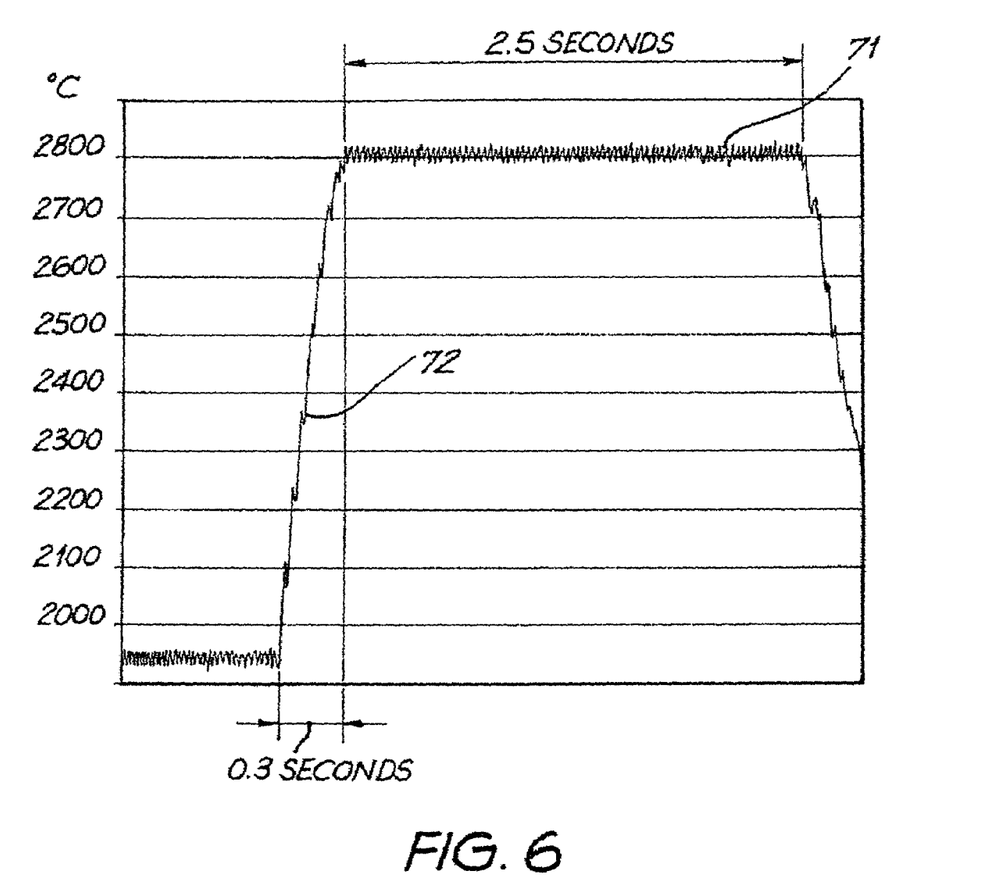
FIG. 6 illustrates the thermal profile for plasma ablation.

The pretreated crucible from step 11 is flash-heated in accordance with the heating profile set out in FIG. 6. to a temperature of 2740-2780° C. (71) for 3 seconds by means of an electronic servo device, which produces a tightly-regulated crucible heating profile featuring a rapid rise time 72 (e.g. 0.3 seconds) followed by a flat plateau 71 maintaining a temperature of approximately 2760° C.±20° C. over the predetermined heating period. These conditions are produced by modifying the electronic controller of the device disclosed in U.S. Pat. No. 5,064,634. The heating regime of the preferred embodiment differs from that of U.S. Pat. No. 5,064,634 in that U.S. Pat. No. 5,064,634 mentions briefly only resistive heating to 2200° C. of a carbon crucible containing a solid radionuclide. In contrast the preferred embodiment process includes preheating of the crucible and carrier removal prior to nanoparticle emission and tight maintenance of the temperature during thermionic plasma induction and particle ablation. The desired operating conditions of the preferred embodiment are shown in Table 3 below:

TABLE 3

| PROCESS COMPONENT | PARAMETER | RANGE | PREFERRED VALUE |
|---|---|---|---|
| Plasma ablation | Argon purge of crucible chamber - flow rate | 2-4 litres/min | 3 litres/min |
| | Crucible temperature rise time for plasma ignition | 0.3-0.7 secs | 0.4 secs |
| | Crucible temperature for plasma ablation | 2740-2780° C. | 2765° C. |
| | Duration of plasma ablation | 2.5-3.5 secs | 3.0 secs |

FIG. 6 shows an actual thermoprofile for regulated AC plasma ablation of a graphite crucible that is held at 2800° C. for 2.5 seconds and shows the rapid rise-time 72 of approximately 0.3 seconds to the full ablation temperature.

The peak current that is required in the present embodiment to achieve the rapid rise to the maximum ablation temperature is 572 amperes, which is reduced to a current of 508 amperes to maintain the temperature during the plateau 71 although it will be appreciated that the actual value of the current will vary from device to device. The temperature is monitored using a calibrated Luxtron optical pyrometer at a wavelength of 950 nm.

Figure 7:
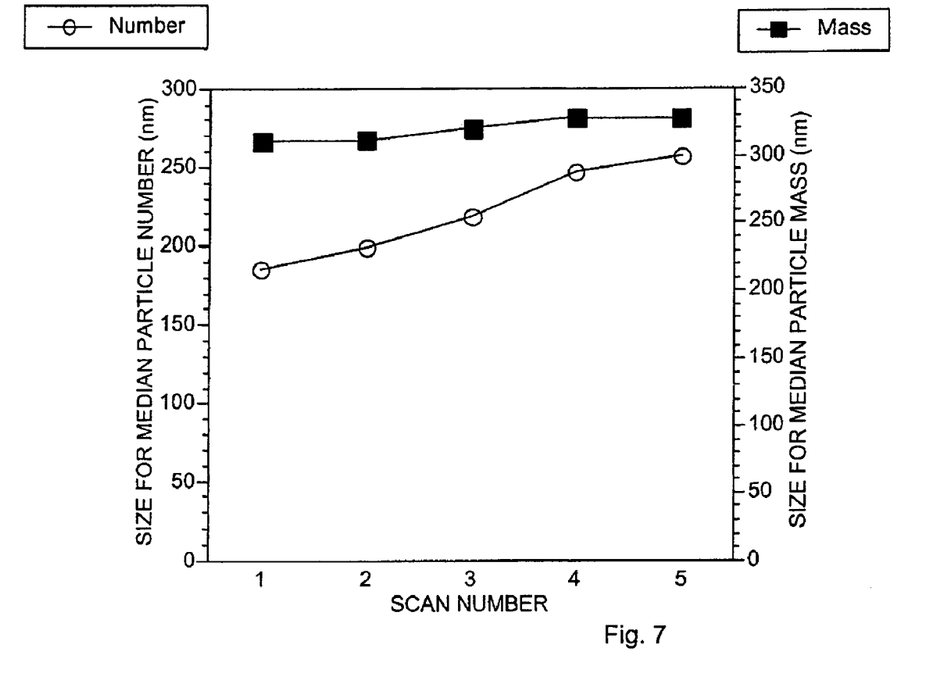
FIG. 7 illustrates the vapour phase characteristics of aerosol produced by the prior art process.
Figure 8:
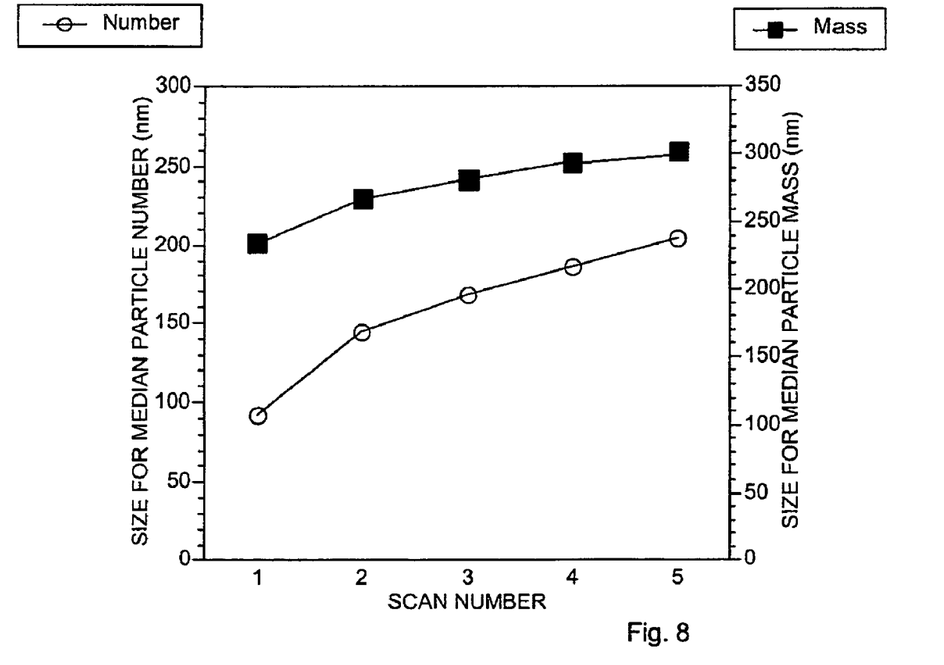
FIG. 8 illustrates the vapour phase characteristics of aerosol produced by the preferred embodiment process.

FIG. 7 and FIG. 8 illustrate a comparison of the resultant vapour phase particle characteristics of aerosols from the prior art and the present process, with FIG. 7 illustrating the results associated with the prior art and FIG. 8 with the present process. The typical values were derived using an electrostatic classifier, particle counter and sizer (TSI Incorporated), to characterise the vapour phase particles in aerosols produced using the prior art technique (FIG. 7) and the technique of the preferred embodiment (FIG. 8). Results are shown for 5 successive scans made on each aerosol preparation; the interval between scans was 40 seconds.

As a first observation, it is found that aerosol from the prior art process produces a visible deposit of white sodium chloride on the 1 micron impact filter placed in the transport line to the instrument, whereas aerosol from the new process did not. The prior art procedure normally retains aerosol in the generator for 3 minutes after crucible ablation, and when the aerosol was released into the particle sizer after this time 50% of the scanned particles were less than 185 nm diameter, and 50% of the scanned mass occurred in particles of less than 311 nm diameter (FIG. 7, scan #1). By contrast, in the preferred embodiment process, aerosol was released from the generator as it was produced and 50% of the emerging particles were less than 92 nm diameter, while 50% of the mass occurred in particles with a diameter of less than 235 nm (FIG. 8, scan #1).

In both cases, the first scan contained the largest number of particles and greatest mass of particulate material; this decayed with successive scans as the gas flow depleted the particles from the chamber. However, there were only 0.55× 109 particles per litre (mass 8.5 μg per litre) in the first scan (scan #1 of FIG. 7), compared to 5.8×109 per litre (mass 22 μg per litre) in the first scan of the preferred embodiment (scan #1 of FIG. 8). The 10-fold reduction in the number of particles (and a 2.6-fold reduction in the median particle mass) in the prior art aerosol was due to considerable losses in the chamber where the product was retained for 3 minutes prior to particle sizing.

With successive scans, the tendency was for the size and mass of scanned aerosol particles to rise. This was particularly noticeable in the results from the preferred embodiment process, while for the prior art process the particles had already been retained in the generator chamber for three minutes and thus the increase in size that occurred over successive scans is less evident. The change in the particle size is attributable to aggregation of the smaller particles.

In summary, vapour phase analyses found the following significant differences from the prior art:

1) Heavy contamination of large sodium chloride particles was found with the prior art.
2) Approximately 10 times the number of imaging particles can be produced without sodium chloride contamination in the preferred embodiment compared to the prior art process.
3) On average, the particles produced by the preferred embodiment process are of half the diameter of those produced by the prior art process, and provided they are delivered to the patient immediately after production (i.e. with minimal storage time in the generator), the smaller sized particles are better suited to lung imaging techniques.

Methods of Testing the Quality of the End Product

The preferred embodiment provides for quality control of the aerosol product through the following steps introduced at regular intervals to test the equipment:

1) Capture of the resultant carbon-encapsulated radionuclide nanoparticles in an aqueous dispersion by the use of an electrostatic sonicating precipitator (such as that disclosed in U.S. Pat. No. 5,792,241).
2) Testing of the resultant aqueous dispersion for soluble free pertechnetate by thin-layer chromatography (TLC method).
3) Testing of the dispersion for excess carbon by measurement of light scattering (light scattering method).
4) Testing of the dispersion for particle size distribution of radioactivity, using syringe filters with hydrophilic membranes of known pore size (filtration method).

The sonicating precipitator can be operated with the parameters shown in Table 4:

TABLE 4

| PROCESS COMPONENT | PARAMETER | RANGE | PREFERRED VALUE |
|---|---|---|---|
| Precipitator conditions for collection of particles for quality control | High tension applied to platinum needle ion source (anode) | 5-10 kV & limited to 15 μA current | 8 kV sustained at 8 μA leakage |
| | Sonicator crystal frequency | 1.4-1.7 MHz | 1.7 MHz |
| | Sonicator power level | 10-40 W | 20 W |
| | Argon flow through precipitator | 3-6 L/min | 4 L/min |

Using this precipitator, the components of an aerosol output from a generator can be captured in a stable aqueous dispersion that is then suitable for analyses of:

a) soluble free pertechnetate (TLC method),
b) excess carbon (light scattering method), and
c) insoluble particle size (filtration method).

Further, the repeated TLC measurement of soluble pertechnetate after standing some hours at ambient temperature, or after autoclaving at 121° C. for 20 minutes also gives a measure of particle stability, which in turn reflects the integrity of the carbon encapsulation of the radionuclide.

The resultant liquid phase properties of aerosol components produced by the prior art process and the preferred embodiment process, analysed after capture in water in an electrostatic precipitator are summarized in Tables 5 and 6 below:

TABLE 5

| Prior Art Process | |
|---|---|
| PERTECHNETATE (% radioactivity) | OTHER PROPERTIES |
| At collection:<br>mean 42%, range 23-69%<br>After autoclaving:<br>mean 61%, range 52-77% | Optical properties: water clear<br>Radioactivity in 220 nm filtrate:<br>mean 67%, range 56-84% |

TABLE 6

| Preferred Embodiment Process | |
|---|---|
| PERTECHNETATE (% radioactivity) | OTHER PROPERTIES |
| At collection:<br>mean 0.9%, range 0.1-5.3%<br>After autoclaving:<br>mean 4.1%, range 0.8-10.3% | Optical properties: v. slight grey turbidity<br>% Radioactivity in 220 nm filtrate:<br>mean 31%, range 18-53% |

In the above measurements, the aerosol from the prior art process was purged from the generator after 3 minutes retention, using 6 minutes of argon flow into the precipitator, maintained at 4 litres per minute. The aerosol from the preferred embodiment was purged from the generator as it was produced, with argon flow into the precipitator also for 6 minutes at 4 litres per minute.

Soluble pertechnetate was determined by a TLC separation of the aqueous particle dispersion, using a stationary phase of silica gel impregnated glass fibre (Gelman) and methyl-ethyl-ketone as the mobile phase. Pertechnetate was measured again with TLC after autoclaving the dispersion for 20 minutes at 121° C. in a sealed vial.

Filtration was performed using syringe filters with hydrophilic mixed cellulose ester (MCE) membranes (Millipore).

Summary of liquid phase properties determined for aerosol preparations:

1) The aerosol produced by the prior art process is heavily contaminated with water-soluble pertechnetate.
2) A significant proportion of the radioactive particles produced by the prior art process has low integrity (less carbon encapsulation), producing significantly more water-soluble pertechnetate after autoclaving.
3) The preferred embodiment process can reduce the soluble pertechnetate contamination of the aerosol by at least a factor of 10.
4) Aerosol particles produced by the new process have greater integrity and release minor amounts of water-soluble pertechnetate on autoclaving.

Overall Conclusion

The preferred embodiment produces a radionuclide aerosol optimised for diagnostic lung imaging. The new process enables very significant and substantial improvements in the quality of the imaging agent including:

1) 90% reduction in the level of contaminating soluble radionuclide.
2) 50% reduction in the peak particle size delivered to the lungs.
3) At least 50% reduction in hospital costs for isotope production.

The preferred embodiment also identifies novel methods for quality control of the imaging agent.

Applying this process to patient diagnostics lowers the radioactive dose needed for each imaging investigation, and reduces the patients' systemic exposure to radioisotope following the procedure.

The forgoing describes preferred features of the present invention. Modifications, obvious to those skilled in the art can be made thereto without departing from the scope of the invention.

We claim:

1. A method for forming an inhalable isotope compound suitable for use in patient medical diagnosis, the method comprising the steps of:
   (a) electrolytically loading a carbon crucible with the isotope via electrolysis from a solvent including the isotope and other contaminants in solution;
   (b) sublimating remaining solvent in the crucible following step (a);
   (c) subsequently ablating the isotope in said carbon crucible, forming an ablation aerosol;
   (d) directly delivering the aerosol for immediate use by a patient.

2. A method as claimed in claim 1 wherein said isotope comprises technetium.

3. A method as claimed in claim 1 wherein the electrolytic flow transitioning the crucible during said electrolytic loading is between 0.1 and 0.7 mL per minute.

4. A method as claimed in claim 1 wherein the current through the carbon crucible during electrolytic loading is between 1 and 10 milliamps.

5. A method as claimed in claim 1 wherein the duration of the electrolytic loading is between 10 and 60 minutes.

6. A method as claimed in claim 1 wherein said isotope solvent contains also a salt.

7. A method as claimed in claim 6 wherein said isotope solvent also contains a salt such as sodium chloride.

8. A method as claimed in claim 1 wherein said sublimation occurs in an argon atmosphere.

9. A method as claimed in claim 8 wherein said sublimation occurs in an argon atmosphere purging a chamber for 2 to 10 minutes.

10. A method as claimed in claim 1 wherein the temperature for sublimation occurs at 1200 to 1800 degrees Celsius.

11. A method as claimed in claim 10 wherein the duration of said sublimation is between 5 and 20 seconds.

12. A method as claimed in claim 1 wherein said ablation occurs in an argon atmosphere.

13. A method as claimed in claim 1 wherein the temperature rise time for ablation is 0.3 to 0.7 seconds.

14. A method as claimed in claim 1 wherein the temperature of said ablation is between 2740 and 2780 degrees Celsius.

15. A method as claimed in claim 1 wherein said ablation occurs for duration of 2.5 to 3.5 seconds.

16. A method as claimed in claim 1 wherein the ablated isotope aerosol is forwarded directly to a patient for medical imaging.

17. A method as claimed in claim 1 wherein said aerosol is periodically subjected to capture in water and analysis to determine the operational efficiency of said method.

18. A method as claimed in claim 17 wherein said analysis includes analysis of free pertechnetate levels or excess carbon levels.

19. A method for forming an inhalable isotope compound suitable for use in patient medical diagnosis, the method including the following steps:

(a) electrolytically loading a carbon crucible with the isotope via electrolysis from a solvent including the isotope and other contaminants in solution; and (b) subsequently sublimating remaining solvent, including dissolved isotope, and salt impurities in the crucible.

20. A method for forming an inhalable isotope compound suitable for use in patient medical diagnosis, the method comprising the steps of:

(a) electrolytically loading a carbon crucible with the isotope, said isotope being precipitated from solution in said carbon crucible via electrolysis; and (b) ablating the isotope electrolytically precipitated in said carbon crucible, forming an ablation aerosol.

21. The method of claim 20, further comprising sublimating any of said solution and any salt impurities remaining in said carbon crucible following step (a) but prior to step (b).

* * * * *